United States Patent [19]

Dockner et al.

[11] Patent Number: 4,481,211
[45] Date of Patent: Nov. 6, 1984

[54] MICROBIOCIDAL SUBSTITUTED BENZYLIMIDAZOLIUM SALTS

[75] Inventors: Toni Dockner, Meckenheim; Ernst-Heinrich Pommer, Limburgerhof; Matthias Wetzler, Ludwigshafen, all of Fed. Rep. of Germany

[73] Assignee: BASF Aktiengesellschaft, Fed. Rep. of Germany

[21] Appl. No.: 441,803

[22] Filed: Nov. 15, 1982

[30] Foreign Application Priority Data

Nov. 20, 1981 [DE] Fed. Rep. of Germany ... 3145927
Nov. 20, 1981 [DE] Fed. Rep. of Germany ... 3145928

[51] Int. Cl.$^3$ .................... A01N 43/50; C07D 233/00
[52] U.S. Cl. ............................. 424/273 R; 548/335; 548/337; 548/346
[58] Field of Search ................ 548/335, 337, 346; 424/273 R

[56] References Cited

U.S. PATENT DOCUMENTS

| | | | |
|---|---|---|---|
| 4,062,965 | 12/1977 | Holtschmidt | 548/335 X |
| 4,095,982 | 6/1978 | Yoneyama et al. | 96/50 PT |
| 4,207,324 | 6/1980 | Matsumura et al. | 424/273 R |
| 4,355,040 | 10/1982 | Furukawa et al. | 424/273 R |

FOREIGN PATENT DOCUMENTS

| | | | |
|---|---|---|---|
| 1216487 | 12/1966 | Fed. Rep. of Germany | 548/335 |
| 2706839 | 8/1978 | Fed. Rep. of Germany | 548/335 |
| 2486079 | 1/1982 | France | 548/335 |

OTHER PUBLICATIONS

Wallhäusser, *Sterilisation-Desinfektion-Konservierung-Chemotherapie*, Thieme Verlag, Stuttgart 1967, pp. 222-223.

*Primary Examiner*—Richard A. Schwartz
*Attorney, Agent, or Firm*—Keil & Weinkauf

[57] ABSTRACT

Substituted benzylimidazolium salts of the formula

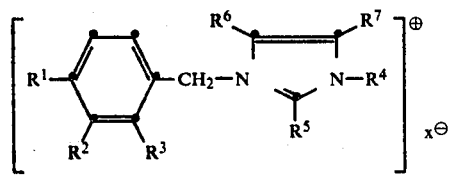

where $R^1$, $R^2$ and $R^3$ are identical or different and are each hydrogen, $C_1$-$C_4$-alkyl or halogen, $R^4$ is alkyl of 8 to 14 carbon atoms or benzyl which is unsubstituted or substituted by halogen or alkyl, $R^5$ is hydrogen, alkyl of 1 to 8 carbon atoms, phenyl or benzyl, $R^6$ is alkyl of 1 to 4 carbon atoms or halogen, $R^7$ is alkyl of 1 to 4 carbon atoms or halogen and X is an anion of an acid, in particular of a hydrohalic acid, and microbicides containing these compounds.

5 Claims, No Drawings

MICROBIOCIDAL SUBSTITUTED BENZYLIMIDAZOLIUM SALTS

The present invention relates to novel, useful substituted benzylimidazolium salts, microbicides containing these compounds, and a method of combating microbes with these compounds.

It has been disclosed that N-dodecyl-N,N-dimethyl-N-benzylammonium chloride (Wallhäusser: Sterilisation-Desinfektion-Konservierung-Chemotherapie, Georg Thieme Verlag, Stuttgart, 1967, page 222) and 1,3-bis-(p-isobutylbenzyl)-imidazolium chloride (German Pat. No. 1,216,487) may be used for combating microbes.

We have found that substituted benzylimidazolium salts of the formula

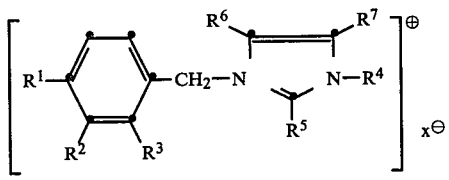

where $R^1$, $R_2$ and $R^3$ are identical or different and are each hydrogen, $C_1$–$C_4$-alkyl or halogen, $R^4$ is alkyl of 8 to 14 carbon atoms or benzyl which is unsubstituted or substituted by halogen or alkyl, $R^5$ is hydrogen, alkyl of 1 to 8 carbon atoms, phenyl or benzyl, $R^6$ is alkyl of 1 to 4 carbon atoms or halogen, $R^7$ is alkyl of 1 to 4 carbon atoms or halogen and X is an anion of an acid, in particular of a hydrohalic acid, possess very good activity against bacteria, fungi and algae.

$C_1$–$C_4$-alkyl is, for example, methyl, ethyl, n-butyl, or t-butyl. $R^4$ is, for example, octyl, decyl, dodecyl, benzyl, 2-methyl-4-chlorobenzyl, 2-methyl-3,4-dichlorobenzyl or 2-methyl-3-chlorobenzyl. Halogen is, for example, chlorine, bromine or iodine.

Alkyl of 1 to 8 carbon atoms is, for example, methyl, ethyl, hexyl or octyl.

Examples of anion are the anions of inorganic or organic acids, such as hydrochloric acid, hydrobromic acid, dodecylbenzenesulfonic acid, acetic acid, salicylic acid or benzoic acid. The salts of hydrohalic acids are preferred.

The novel compounds are prepared, for example, by a method wherein a compound of the formula

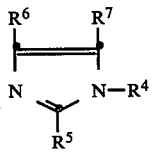

where $R^4$, $R^5$, $R^6$ and $R^7$ have the above meanings, is reacted, in the melt, with a compound of the formula

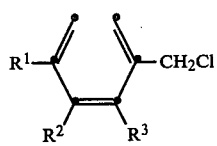

where $R^1$, $R^2$ and $R^3$ have the above meanings. For example, the starting compounds may be employed in stoichiometric amounts, and the reaction carried out with molten imidazole in the absence of a solvent. Depending on the melting point, the reaction is carried out at from about 50° to 130° C.

EXAMPLE 1

Preparation of 1-dodecyl-3-[2-methyl-4-chlorobenzyl]-4-methyl-5-iodoimidazolium chloride 37.9 g (0.1 mole) of 1-dodecyl-4-methyl-5-iodoimidazole were initially introduced, and heated to 100° C., 17.7 g (0.1 mole) of 4-chloro-o-xylyl chloride were added dropwise, and the reaction mixture was stirred further at 120°–130° C. A compound (compound No. 7) of the formula

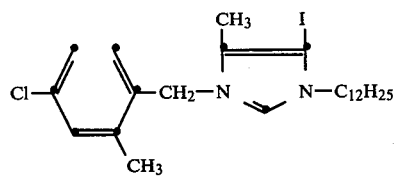

was obtained.

| | Analysis: | |
|---|---|---|
| | calculated: | found: |
| C | 51.98 | 52.7 |
| H | 6.67 | 7.1 |
| N | 5.05 | 5.2 |
| Cl | 12.81 | 12.1 |
| I | 23.46 | 22.7 |

EXAMPLE 2

Preparation of 1-decyl-3-[2-methyl-3-chlorobenzyl]-4-methyl-5-bromoimidazolium chloride 60.2 g (0.2 mole) of 1-decyl-4-methyl-5-bromoimidazole were heated to 100° C., and 35.4 g (0.2 mole) of 3-chloro-o-xylyl chloride were added dropwise, and the reaction mixture was stirred for a further 30 minutes at 120°–130° C.

The liquid compound (compound No. 8) gave the following analysis:

| | Analysis: | |
|---|---|---|
| | calculated: | found: |
| C | 55.46 | 56.1 |
| H | 6.93 | 7.2 |
| N | 5.88 | 5.9 |
| Cl | 14.91 | 14.1 |
| Br | 16.81 | 15.9 |

EXAMPLE 3

Preparation of 1,3-di-[2-methyl-4-chlorobenzyl]-4-methyl-5-chloroimidazolium chloride 255 g (1 mole) of 1-[2-methyl-4-chlorobenzyl]-4-methyl-5-chloroimidazole were heated to 80° C., 175 g (1 mole) of 4-chloro-o-xylyl chloride (2-methyl-4-chlorobenzyl chloride) were added dropwise, and the mixture was then stirred further for about 1 hour at this temperature.

430 g of a compound (compound No. 6) of the following composition were formed:

|   | found: | calculated: |
|---|---|---|
| C | 56.5% | 55.81% |
| H | 5.0% | 4.65% |
| N | 6.8% | 6.51% |
| Cl | 32.1% | 33.0% |

EXAMPLE 4

Preparation of 1-decyl-3-[2-methyl-4-chlorobenzyl]-4-methyl-5-chloroimidazolium chloride 25.6 g (0.1 mole) of 1-decyl-4-methyl-5-chloroimidazole were heated to 100° C., 17.7 g (0.1 mole) of 4-chloro-o-xylyl chloride were added dropwise, and the mixture was stirred for a further 30 minutes at 125° C.

43 g of a compound of melting point 99° C. were formed (compound No. 3).

EXAMPLE 5

Preparation of 2-dodecyl-3-[2-methyl-3-chlorobenzyl]-4-methyl-5-chloroimidazolium chloride 14.2 g (0.05 mole) of 1-dodecyl-4-methyl-5-chloroimidazole were heated to 95° C., 8.4 g (0.05 mole) of 3-chloro-o-xylyl chloride were added dropwise, and the mixture was stirred for a further 30 minutes at 95° C.

22.6 g of end product of melting point 112° C. were formed (compound No. 5). The yields were quantitative.

EXAMPLE 6

Preparation of 1-decyl-3-benzyl-4-methyl-5-chloroimidazolium chloride 25.5 g (0.1 mole) of 1-decyl-4-methyl-5-chloroimidazole were heated to 100° C., 12.6 g (0.1 mole) of benzyl chloride were added dropwise in the course of 10 minutes, and the mixture was then stirred for a further 30 minutes at 125° C.

38 g (0.1 mole) of end product (compound No. 1) were obtained. The yields were quantitative.

Those compounds in the table below which are given together with their melting points (mp) were prepared similarly.

Their structures were determined by elementary analysis. The compounds for which no physicochemical data are given may be obtained in the same manner as those which have actually been prepared; they may be expected to have actions similar to those of the compounds which have been investigated in detail, since their structures are similar.

| Active ingredient No. | $R^1$ | $R^2$ | $R^3$ | $R^4$ | $R^5$ | $R^6$ | $R^7$ | X | mp. |
|---|---|---|---|---|---|---|---|---|---|
| 1 | H | H | H | $C_{10}H_{21}$ | H | $CH_3$ | Cl | Cl | |
| 2 | H | Cl | $CH_3$ | $C_{10}H_{21}$ | H | $CH_3$ | Cl | Cl | 125° C. |
| 3 | Cl | H | $CH_3$ | $C_{10}H_{21}$ | H | $CH_3$ | Cl | Cl | 99° C. |
| 4 | Cl | H | $CH_3$ | $C_{12}H_{25}$ | H | $CH_3$ | Cl | Cl | |
| 5 | H | Cl | $CH_3$ | $C_{12}H_{25}$ | H | $CH_3$ | Cl | Cl | 112° C. |
| 6 | Cl | H | $CH_3$ | 2-$CH_3$—4-Cl—benzyl | H | $CH_3$ | Cl | Cl | |
| 7 | Cl | H | $CH_3$ | $C_{12}H_{25}$ | H | $CH_3$ | I | Cl | |
| 8 | Cl | H | $CH_3$ | $C_{10}H_{21}$ | H | $CH_3$ | Br | Cl | |
| 9 | H | H | Cl | $C_{10}H_{21}$ | H | $CH_3$ | Br | Cl | |
| 10 | Cl | H | H | $C_{10}H_{21}$ | H | $CH_3$ | Br | Cl | |
| 11 | H | H | Cl | $C_{12}H_{25}$ | H | $CH_3$ | I | Cl | |
| 12 | Cl | H | H | $C_{12}H_{25}$ | H | $CH_3$ | I | Cl | |

The starting materials of the formula

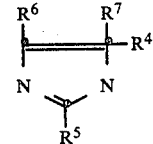

where $R^4$, $R^5$, $R^6$ and $R^7$ have the above meanings, are prepared by methods in which a compound of the formula

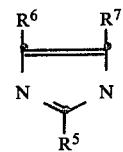

where $R^5$, $R^6$ and $R^7$ have the above meanings, is reacted with $NaOCH_3$, in a solvent, eg. dimethylformamide, at from 100° to 150° C. in the course of from 1 to 20 hours, the $CH_3OH$ is distilled off, the product thus obtained is reacted with a compound of the formula $R^4$-Cl where $R^4$ has the above meanings, the NaCl is separated off from the reaction mixture, and the end product is isolated from the solvent.

For example, the following compounds are obtained in this manner:

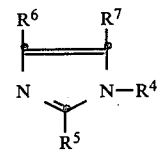

| $R^4$ | $R^5$ | $R^6$ | $R^7$ | boiling range |
|---|---|---|---|---|
| $C_{10}H_{21}$ | H | $CH_3$ | Cl | 178–211° C./8 mbar |
| $C_{12}H_{23}$ | H | $CH_3$ | Cl | 175–221° C./8 mbar |

The starting material of the formula

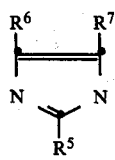

where $R^5$, $R^6$ and $R^7$ have the above meanings, is prepared by a method in which, for example, 4-methylimidazole is reacted with chlorine gas in ultraviolet light at from 20° to 50° C., in a solvent, eg. carbon tetrachloride or monochlorobenzene, for from 2 to 10 hours, to give the hydrochloride of 4-methyl-5-chloroimidazole, which is converted to the free base using an alkali, eg. $NaHCO_3$.

The compound melts at 130°–132° C.

The novel compounds are useful for combating microorganisms (microbes), for example for the protection of water against attack by algae, and for combating slime-forming microorganisms in recooling plant, in the paper industry and in humidifier plant. They may furthermore be employed as disinfectants or preservatives in industry and as bactericides in plant protection.

The following microorganisms may, for example, be combated with the novel active ingredients: *Staphylococcus aureus, Escherichia coli, Klebsiella pneumoniae, Citrobacter freundii, Proteus vulgaris, Pseudomonas aeruginosa, Pseudomonas fluorescens, Xanthomonas vesicatoria, Xanthomonas malvacearum, Erwinia carotovora, Erwinia amylovora, Desulfovibrio desulfuricans, Streptoverticillium rubrireticuli, Aspergillus niger, Aspergillus versicolor, Penicillium funiculosum, Paecilomyces variotii, Trichoderma viride, Chaetomium globosum, Candida albicans, Geotrichum candidans, Monilia sitophila, Scenedesmus quadricauda, Chlorella vulgaris* and *Nostoc muscorum*.

The novel compounds are readily soluble in water, and are therefore preferably employed in the form of aqueous solutions. Concentrated formulations may also be prepared using organic solvents, e.g. ethanol.

The active ingredient is conventionally used in a concentration of from 0.01 to 1%, based on the weight of the material to be protected; when employed for the treatment of water in oil recovery, in swimming pools, recooling plant, humidifier plant or flower preservatives or in the paper industry, amounts of active ingredient of from 5 to 100 ppm are sufficient to suppress the development of microorganisms. Ready-to-use disinfectant solutions contain from 0.5 to 10% by weight of active ingredient.

In plant protection, the active ingredient is used in an amount of from 0.1 to 5 kg per hectare. Formulations with organic solvents can contain from 1 to 60% of active ingredient.

The active ingredients may also be mixed with other conventional microbicides. In many cases, this increases the spectrum of microbicidal action, and a number of these mixtures exhibit synergistic effects, i.e. the microbicidal activity of the combination is greater than the sum of the activity of the individual components.

Examples of active ingredients which may be combined with the novel benzylimidazoles are 2-(thiocyanomethylthio)-benzothiazole, 1-[2-(2,4-dichlorophenyl-2-(propenyloxy)-ethyl]-1H-imidazole, 2,4,5,6-tetrachloroisophthalodinitrile, methylene bisthiocyanate, tributyl-tin oxide, mercaptobenzothiazole, benzoisothiazolone and its alkali metkal salts, alkali metal compounds of N'-hydroxy-N-cyclohexyldiazenium oxide, 2-(methoxycarbonylamino)benzimidazole, 2-methyl-3-oxo-5-chlorothiazolin-3-one, trihydroxymethylnitromethane, glutarodialdehyde, chloroacetamide and quaternary ammonium compounds.

In the experiments below, the following conventional active ingredients were used as comparative substances:

A: N-dodecyl-N,N-dimethyl-N-benzylammonium chloride (Wallhäusser: Sterilisation-Desinfektion-Konservierung-Chemotherapie, Georg Thieme Verlag, Stuttgart, 1967, page 222)

B: 1,3-bis-(p-isobutylbenzyl)-imidazolium chloride (German Pat. No. 1,216,487).

EXPERIMENT 1

To determine the activity of the novel compounds against bacteria, 5 ml of doubly concentrated nutrient broth are added to 5 ml portions, of increasing dilution, of the active ingredients, in sterile test tubes, and the components are mixed. The mixtures in the tubes are then inoculated by adding one drop of a 16-hour old broth culture, diluted in the ratio 1:10, of bacteria of the species *Escherichia coli*, and incubation is carried out for 24 hours at 37° C. After this period, samples are transferred from the tubes to nutrient media suitable for bacteria, and these are also incubated for 24 hours at 37° C. The dilution at which development of bacteria no longer takes place after a sample has been transferred to the nutrient medium is given as the lethal concentration.

The result of the experiment shows that, in their bactericidal action against Escherichia, for example, the compounds 2, 3, 4, 5, 9, 10, 11 and 12 (for example 12:1 million parts by weight dilution) are superior to the conventional active ingredient B (for example 100:1 million).

EXPERIMENT 2

To test the activity against fungi, the active ingredients are added to a nutrient solution suitable for the growth of the fungi *Aspergillus niger, Oidium lactis* or *Candida albicans*, the amounts of active ingredient used being 100, 50, 25, 12, 6 and 3 parts by weight per million parts of nutrient solution. 10 ml portions of nutrient solution/active ingredient mixture are introduced into sterile test tubes and inoculated with one drop of a spore suspension which contains $10^6$ conidia or cells. After incubation for 120 hours, samples are taken from those tubes in which no visible fungal growth has taken place, and transferred to nutrient media suitable for fungi. The dilution at which fungal growth no longer takes place, after a sample has been transferred to the nutrient medium, is determined.

The result of the experiment shows that in respect of their fungicidal action, for example, the compounds 1, 2, 3, 4, 5, 9, 10, 11 and 12 (for example 12:1 million dilution) are superior to the conventional active ingredients A and B (for example 25:1 million).

EXPERIMENT 3

To test the activity against green algae, the active ingredients are added to a phosphate-rich nutrient solution which promotes reproduction of the unicellular green algae *Chlorella vulgaris* and has beforehand been inoculated with a suspension which contains $10^6$ cells of this algae per ml of nutrient solution. The active ingredient is used in amounts of 10, 7.5, 5, 2.5 and 1 parts by weight per million parts of nutrient solution. 100 ml portions of nutrient solution/active compound mixture, as well as nutrient solution alone (control), are introduced into 300 ml glass flasks. The mixtures are exposed to light at room temperature for 10 days, after which the activity is assessed.

The result of the experiment shows that in respect of their algicidal action, for example, the compounds 2 and 3 (for example 2.5:1 million dilution) are superior to the conventional active ingredients A and B (for example 5:1 million).

We claim:

1. A substituted benzylimidazolium salt of the formula

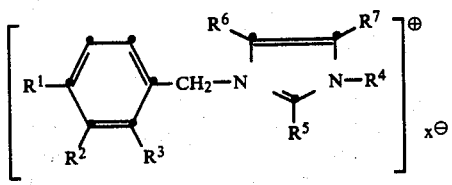

where $R^1$ and $R^2$ are identical or different and each denotes hydrogen or chlorine; $R^3$ is methyl; $R^4$ is alkyl of 8 to 14 carbon atoms or benzyl which is unsubstituted or substituted by halogen or alkyl, $R^5$ is hydrogen, $R^6$ is methyl; $R^7$ is halogen and X is an acid anion.

2. A compound as described in claim 1, wherein $R^4$ is decanyl or dodecanyl, $R^7$ is chlorine and X is chloride.

3. A microbicide composition which contains a solid or liquid carrier and an effective amount of a benzylimidazolium salt of the formula

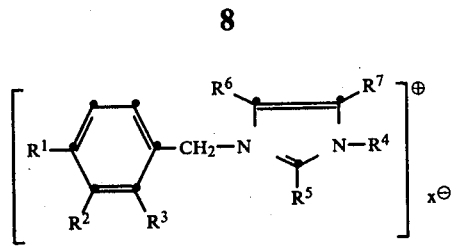

where $R^1$ and $R^2$ are identical or different and each denotes hydrogen or chlorine; $R^3$ is methyl; $R^4$ is alkyl of 8 to 14 carbon atoms or benzyl which is unsubstituted or substituted by halogen or alkyl, $R^5$ is hydrogen, $R^6$ is methyl; $R^7$ is halogen and X is an acid anion.

4. A microbicide composition as described in claim 3, wherein $R^4$ is decanyl or dodecanyl, $R^7$ is chlorine and X is chloride.

5. A process for combating microbes, wherein the microbes, or the articles to be protected from attack by microbes, are treated with an effective amount of an N-benzylimidazolium salt of the formula

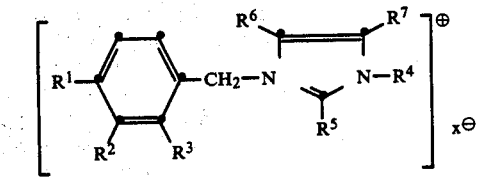

where $R^1$ and $R^2$ are identical or different and each denotes hydrogen or chlorine; $R^3$ is methyl; $R^4$ is alkyl of 8 to 14 carbon atoms or benzyl which is unsubstituted or substituted by halogen or alkyl, $R^5$ is hydrogen, $R^6$ is methyl; $R^7$ is halogen and X is an acid anion.

* * * * *